US010485650B2

(12) United States Patent
Kölbel

(10) Patent No.: US 10,485,650 B2
(45) Date of Patent: Nov. 26, 2019

(54) ENDOLUMINAL PROSTHESIS

(71) Applicant: COOK MEDICAL TECHNOLOGIES LLC, Bloomington, IN (US)

(72) Inventor: Tilo Kölbel, Hamburg (DE)

(73) Assignee: Cook Medical Technologies LLC, Bloomington, IN (US)

(*) Notice: Subject to any disclaimer, the term of this patent is extended or adjusted under 35 U.S.C. 154(b) by 57 days.

(21) Appl. No.: 15/654,160

(22) Filed: Jul. 19, 2017

(65) Prior Publication Data
US 2019/0021839 A1 Jan. 24, 2019

(51) Int. Cl.
| A61F 2/24 | (2006.01) |
| A61F 2/07 | (2013.01) |
| A61F 2/89 | (2013.01) |
| A61F 2/966 | (2013.01) |
| A61F 2/30 | (2006.01) |
| A61F 2/95 | (2013.01) |
| A61F 2/06 | (2013.01) |

(52) U.S. Cl.
CPC .............. *A61F 2/07* (2013.01); *A61F 2/2412* (2013.01); *A61F 2/2418* (2013.01); *A61F 2/2436* (2013.01); *A61F 2/89* (2013.01); *A61F 2/966* (2013.01); *A61F 2/2427* (2013.01); *A61F 2/2439* (2013.01); *A61F 2002/061* (2013.01); *A61F 2002/075* (2013.01); *A61F 2002/30092* (2013.01); *A61F 2002/9522* (2013.01); *A61F 2240/001* (2013.01); *A61F 2250/0063* (2013.01)

(58) Field of Classification Search
CPC .................. A61F 2/07; A61F 2002/075; A61F 2002/067; A61F 2002/061; A61F 2/2418; A61F 2002/828; A61F 2/2439
See application file for complete search history.

(56) References Cited

U.S. PATENT DOCUMENTS

| 2008/0275548 A1 | 11/2008 | Svensson |
| 2014/0316513 A1 | 10/2014 | Tang |
| 2016/0235525 A1* | 8/2016 | Rothstein .............. A61F 2/2418 |

FOREIGN PATENT DOCUMENTS

| EP | 1245202 A1 | 10/2002 |
| WO | WO 98/53761 | 12/1998 |

OTHER PUBLICATIONS

International Search Report and Written Opinion for corresponding PCT/2018/042393, dated Oct. 11, 2018, 16 pages.

* cited by examiner

*Primary Examiner* — Suba Ganesan
(74) *Attorney, Agent, or Firm* — Brinks Gilson & Lione

(57) ABSTRACT

The present embodiments provide an endoluminal prosthesis having a stent-graft portion with a superior end and an inferior end and a graft portion. The graft portion is attached to the stent-graft portion at a junction, and the graft portion extends inferiorly from the junction in a pre-delivery configuration. In a first delivered configuration, the stent-graft portion is radially expanded, and in a second delivered configuration, the graft portion is everted and moved superiorly relative to the pre-delivery configuration. A valve may be attached to the graft portion when the graft portion is in the pre-delivery configuration. When delivered, the stent-graft portion is deployed first, and the graft portion and attached valve are then moved superiorly, with at least a portion of the graft portion extending superiorly beyond the superior end of the stent-graft portion.

11 Claims, 9 Drawing Sheets

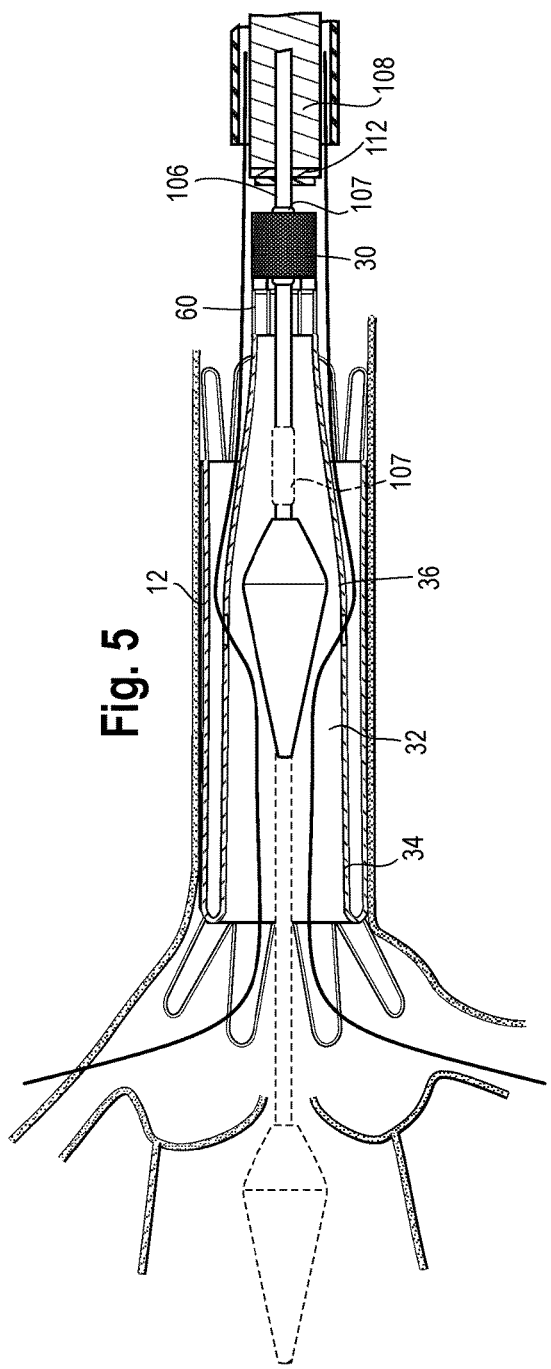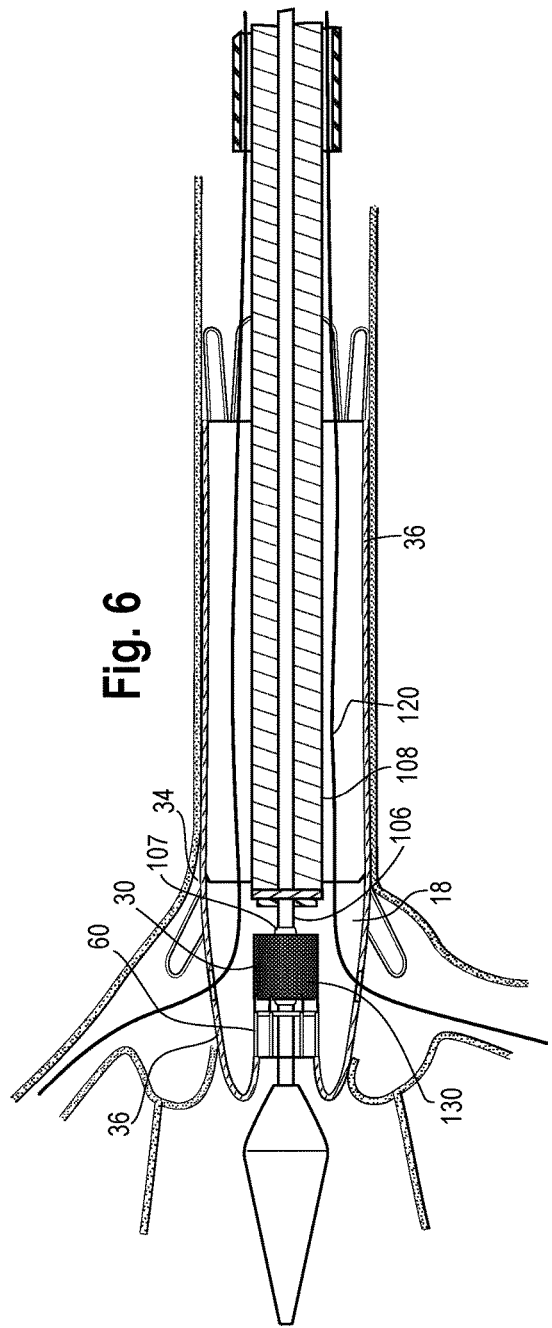

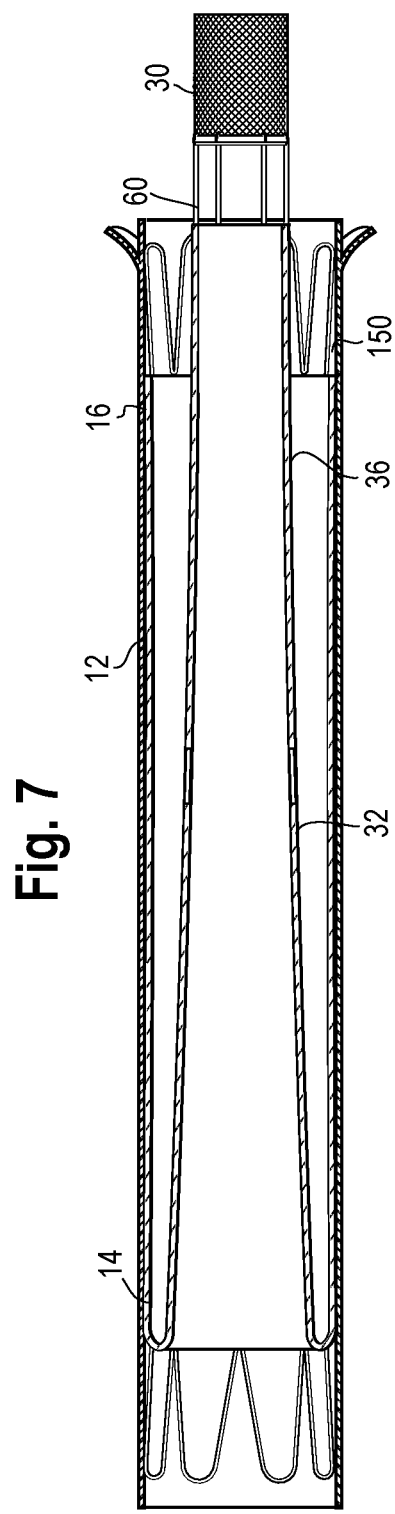

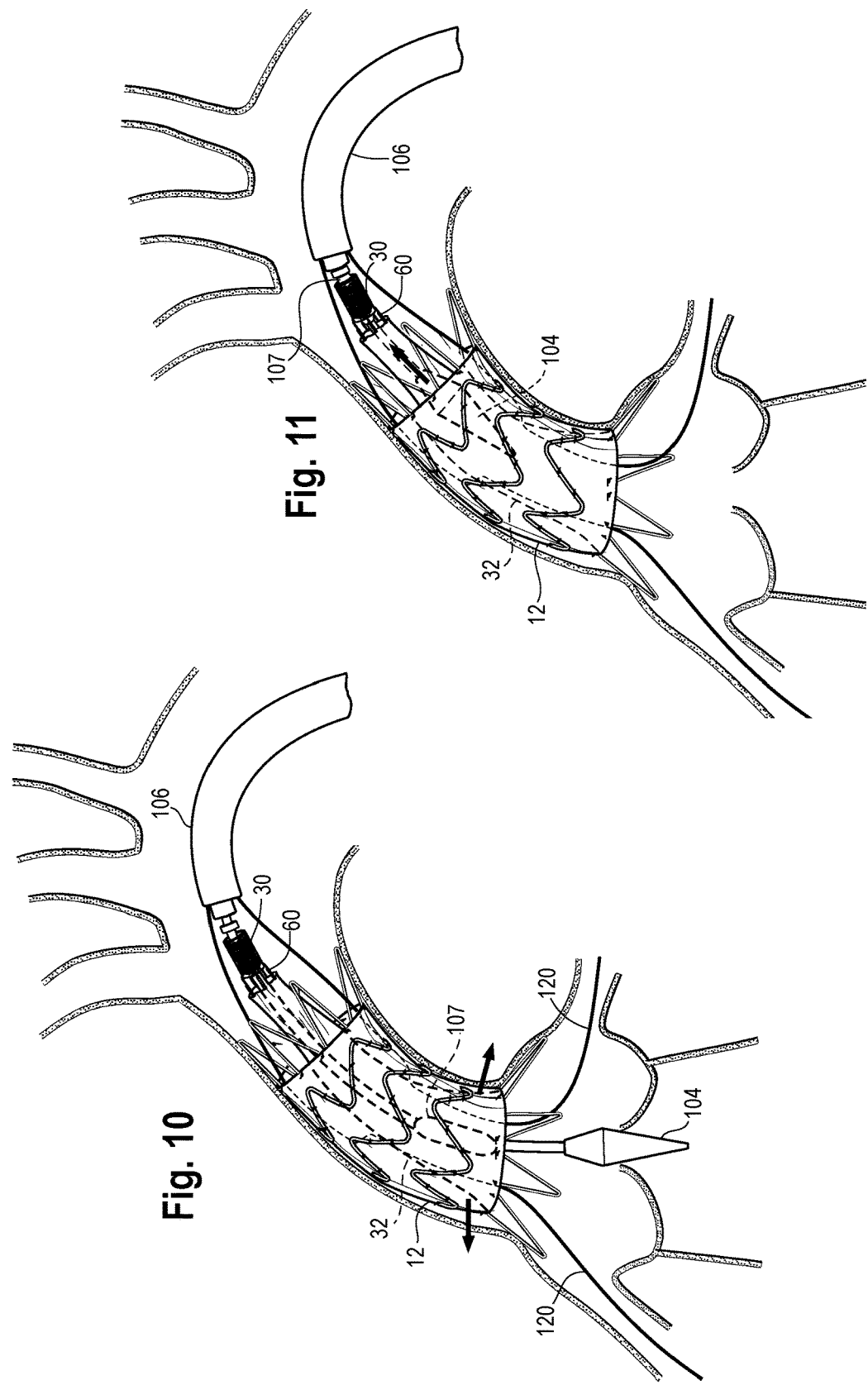

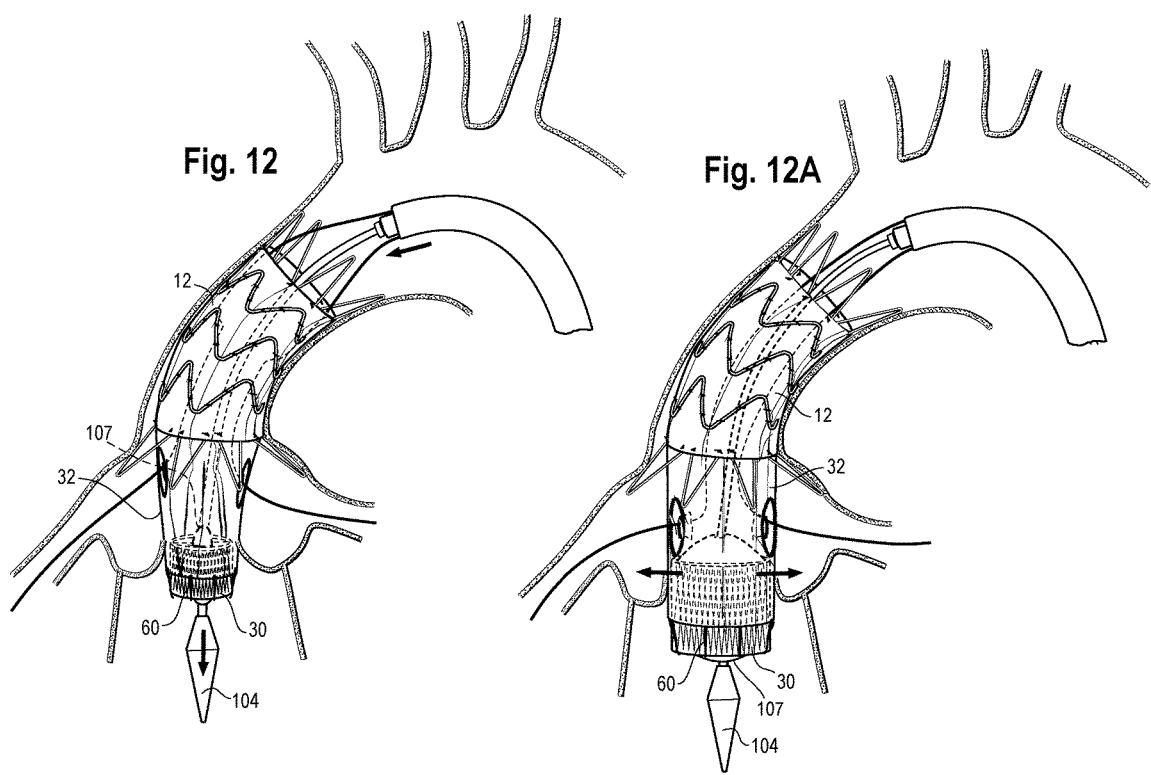

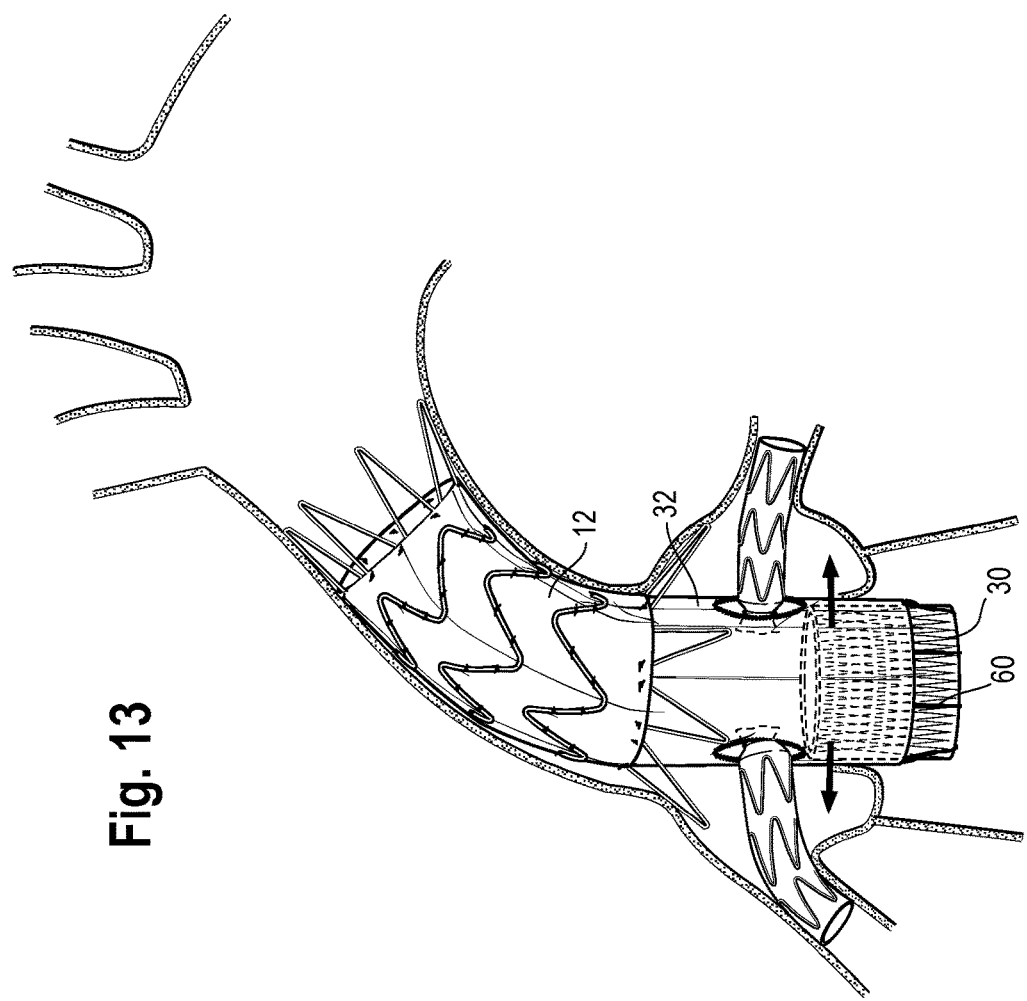

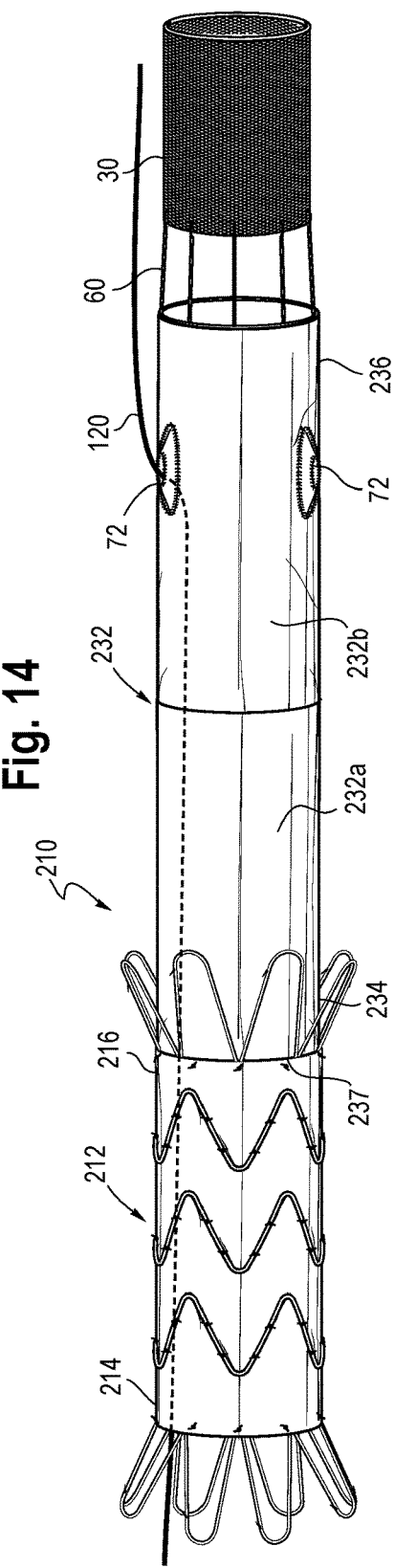
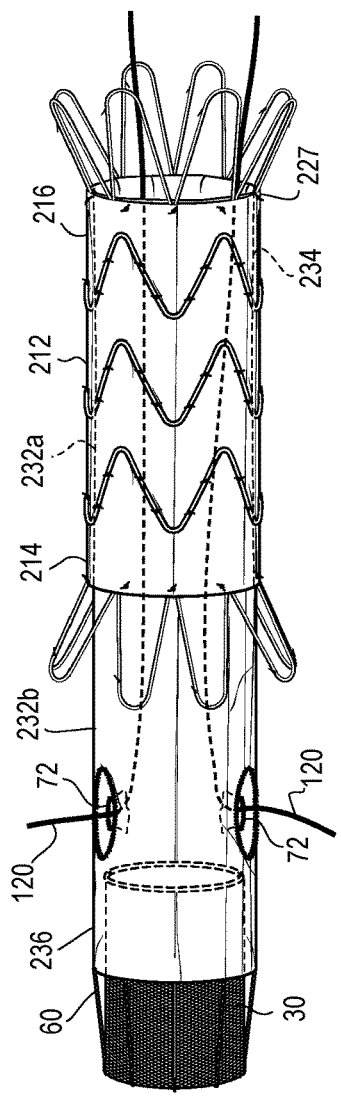
Fig. 14
Fig. 15

ENDOLUMINAL PROSTHESIS

BACKGROUND

The present embodiments relate generally to an endoluminal prosthesis including a valve and a delivery system for delivering and deploying the prosthesis and valve.

Stent grafts and valves are used to treat aortic disease in the ascending aorta and the aortic valve. In such instances when repair of both the ascending aorta and the aortic valve is involved, cardiac or vascular surgeons or interventional cardiologists will typically utilize open surgery to perform such repairs for most patients. Endovascular repair, such as Transcatheter Aortic Valve Replacement (TAVR) is possible for some patients to repair the aortic valve. TAVR may be preferable for some patients who are not candidates for open surgery or are high risk for open surgery. However, traditional endovascular procedures can be difficult to deploy both a graft for the ascending aorta as well as an aortic valve.

In typical endovascular delivery of stent grafts, stent grafts may be deployed by accessing a vasculature with a small incision in the skin and guiding a delivery system through the vasculature to the target area. This intraluminal delivery is less invasive and generally preferred over more intrusive forms of surgery such as open surgery. Multiple stent grafts or other components may be implanted using intraluminal delivery to provide a system of interconnected stent grafts and components. Interconnected stent grafts can be made of fenestrated stent grafts and smaller side branch stent grafts.

In some conditions, an aneurysm has engulfed a main vessel as well as the aortic valve or other nearby portions of the vasculature. In this case, the aortic valve and the ascending aorta require repair.

In the transfemoral approach, the delivery system is introduced toward the heart and up through the ascending aorta via the femoral artery. The aortic valve replacement is deployed more superior to the heart than the ascending aorta graft, and therefore must typically be delivered prior to the ascending aorta graft. One such procedure could include sequential delivery, such that the aortic valve is delivered first, followed by delivery of the ascending aorta graft.

SUMMARY

The present embodiments provide a prosthesis for being placed within a patient's vasculature. The prosthesis has an expandable stent-graft portion having a superior end and an inferior end. The superior end is that which is closest to the heart when in place within the vasculature and may also be referred to as an inflow end. The inferior end is that part placed further from the heart and may be referred to as the outflow end. The stent-graft portion may have a lumen extending between the superior and inferior ends. A flexible graft portion may have a tubular sidewall and an inferior end and a superior end after delivery and deployment within the vasculature, where the inferior end is attached to the superior end of the stent-graft portion. A mounting frame may be coupled to the superior end of the graft portion. The mounting frame is configured to receive and mount a valve, such as an aortic valve, thereto.

The prosthesis may have a pre-delivery configuration, a first delivered condition, and a second delivered condition. The pre-delivery configuration is a configuration prior to delivery into the vasculature of a patient, and the first and second delivered configurations are configurations after delivery of the prosthesis to the vasculature of the patient, where the second delivered configuration succeeds the first delivered configuration.

The prosthesis may include at least one perfusion port between the superior and inferior ends of the graft portion. The stent-graft portion may extend from the inferior end of the graft portion in the second delivered configuration and have a superior end coincident with the inferior end of the graft portion to form a graft portion/stent graft portion junction, a stent-graft inferior end, and an internal lumen. In the second delivered configuration the inferior end of the stent graft may be the outflow end of the prosthesis.

In the pre-delivery configuration, the graft portion may be inverted into the lumen of the stent graft portion such that the mounting frame is located at the inferior opening of the stent graft portion and the prosthesis is in a compressed configuration.

In the first delivered configuration, the stent graft portion may be expanded and the graft portion is configured to be everted out of the superior end of the stent graft portion after expansion of the stent graft portion.

In one approach, in the first delivered configuration and the pre-delivery configuration, at least a portion of the mounting frame extends out of the stent-graft portion from the inferior end opening of the stent-graft portion.

The at least one perfusion port may provide fluid communication radially through a sidewall of the graft portion and arranged in the graft portion to provide perfusion to an adjacent body vessel from the interior of the prosthesis in the second delivered configuration. In the pre-delivery configuration and the first delivered configuration, the at least one perfusion port may be disposed within the lumen of the stent-graft portion and, in the second delivered configuration, the at least one perfusion port is disposed outside of the lumen of the stent-graft portion and superior from the stent-graft portion to provide fluid communication between outside of the graft portion to inside of the graft portion and the lumen of the stent-graft portion.

In the second delivered configuration, the graft portion may define a graft portion lumen that connects to the lumen of the stent-graft portion to define an extended lumen.

In one aspect, the prosthesis may include a peel-away sheath that houses the stent-graft portion and graft portion in the pre-delivery configuration.

In one form, a tubular sidewall of the graft portion may have a first tubular surface and a second tubular surface extending between the superior and inferior ends of the graft portion and, in the first delivered configuration, the first tubular surface is radially inward from the second tubular surface and, in the second delivered configuration, the first tubular surface is radially outward from the second tubular surface.

In one approach, the prosthesis may include an aortic valve connected to the mounting frame in the pre-delivery configuration. In the second delivered configuration, the aortic valve may be disposed at least partially within the tubular sidewall of the graft portion. The mounting frame may define at least one opening therethrough that provides fluid communication through the superior end of the graft portion in the first delivered configuration.

In one form, the prosthesis may further include at least one preloaded wire in the first delivered configuration extending into the stent-graft portion through the inferior end opening of the stent-graft portion radially between the stent-graft portion and the graft portion, through the at least one passageway and the tubular sidewall of the graft portion, and out through the superior end opening of the graft portion and the superior end of the stent-graft.

In another aspect, a method of delivering an endoluminal prosthesis to a blood vessel is provided. The method includes delivering an endoluminal prosthesis that may include an expandable stent-graft portion having a superior end and an inferior end, the stent-graft portion defining a lumen extending between the superior and inferior ends. The prosthesis may further include a flexible graft portion having a tubular sidewall and having a first end and a second end, the first end attached to the expandable stent-graft at a junction.

The prosthesis may further include a mounting frame coupled to the second end of the graft portion, the mounting frame configured to receive and mount a valve thereto. The mounting frame may be disposed at the inferior end of the stent-graft portion in a pre-delivery configuration of the prosthesis. The graft portion may extend in an inferior direction from the junction in the pre-delivery configuration, with the stent-graft portion and the graft portion compressed in the pre-delivery configuration.

The prosthesis may further include a first delivered configuration and a second delivered configuration, wherein the pre-delivery configuration is a configuration prior to delivery into the vasculature of a patient, and the first and second delivered configurations are configurations after delivery of the prosthesis to the vasculature of the patient, where the second delivery configuration succeeds the first delivery configuration.

The method may further include advancing the endoluminal prosthesis in an insertion direction toward a target site and locating the stent graft in a first position at the target site. The method may further include expanding the stent-graft radially outward into engagement with a vessel wall and into the first delivered configuration, where the stent-graft is radially expanded.

The method may further include moving the second end of the flexible graft portion in an insertion direction toward the heart while the first end of the flexible graft portion remains attached to the stent-graft at the junction. Moving the second end in the insertion direction results in everting the flexible graft portion and positioning the mounting frame superiorly from the superior end of the stent-graft portion into the second delivered configuration.

In one form, an aortic valve is attached to the mounting frame in the pre-delivery configuration. The method may include expanding the aortic valve after positioning the mounting frame superior from the superior end of the stent-graft in the second delivered configuration.

The flexible graft portion may include one or more passageways through a sidewall of the graft portion, and the method may include delivering a branch extension prosthesis to the passageway to provide fluid communication between opposite sides of the sidewall when the prosthesis in the second delivered configuration.

In another example, a system for delivering an endoluminal prosthesis to a blood vessel is provided. The system may include a delivery sheath having an insertion end and an operator end and a lumen extending therebetween. The system may further include a dilator tip coupled to the insertion end of the delivery sheath and a delivery catheter extending through the lumen of the delivery sheath.

The system may further include a prosthesis including a stent-graft portion having a superior end and an inferior end, the superior end configured to lie closest to a heart of a patient in a body vessel and the inferior end configured to lie further from the heart of the patient in the body vessel, such that the superior end of the stent-graft portion is an inflow end of the stent-graft portion. The prosthesis may further include a flexible graft portion attached to the stent-graft portion at a junction.

The prosthesis may have a pre-delivery configuration, a first delivered configuration, and a second delivered configuration. In the pre-delivery configuration and the first delivered configuration, the prosthesis includes a graft portion disposed within a stent-graft portion, and in the second delivered configuration, the graft portion is everted out of the stent-graft portion.

The pre-delivery configuration is a configuration prior to delivery into the vasculature of a patient, and the first and second delivered configurations are configurations after delivery of the prosthesis to the vasculature of the patient, where the second delivery configuration succeeds the first delivery configuration.

In the pre-delivery configuration and the first delivered configuration, the flexible graft portion extends toward the operator end from the junction, and in the second delivered configuration, the flexible graft portion is everted relative to the pre-delivery configuration and extends from the junction in a direction away from the operator end, and at least a portion of the flexible graft portion extends superiorly beyond the superior end of the stent-graft portion.

The stent-graft portion may be mounted on the delivery catheter with the superior end of the stent-graft disposed adjacent the superior end of the delivery sheath.

The flexible graft portion of the prosthesis may have a tubular sidewall and a first end and a second end, the first end attached to the superior end of the expandable stent-graft. The first end may be an inferior end and the second end may be a superior end when in the second delivered configuration. The first end of the graft portion may be attached to the expandable stent-graft at the junction between the graft portion and the stent-graft portion in the pre-delivery configuration, the first delivered configuration, and the second delivered configuration.

A mounting frame may be coupled to the second end of the graft portion, the mounting frame configured to receive and mount a valve thereto. The mounting frame may be disposed inferiorly from the superior end of the stent-graft portion in the pre-delivery configuration and the first delivered configuration, and the mounting frame is disposed superiorly from the superior end of the stent-graft portion in the second delivered configuration.

In the pre-delivery configuration, the second end of the graft portion is disposed inferior from the junction. In the first delivered configuration, the stent-graft portion may be radially expanded relative to the pre-delivery configuration. In the second delivered configuration, the graft portion is everted relative to the pre-delivery configuration, and the second end of the graft portion and the mounting frame are disposed superiorly from the stent-graft portion, and at least a portion of the graft portion is disposed longitudinally superior to the stent-graft portion.

In the first delivered configuration, the superior end of the stent-graft portion may define an inflow end of the prosthesis and the second end of the flexible graft portion defines an outflow end of the prosthesis, such that blood flowing through the superior end of the stent-graft portion toward the inferior end of the stent-graft portion will flow through the superior end of the stent-graft portion before flowing past the second end of the graft portion. In the second delivered configuration, the second end of the graft portion may define the inflow end, such that blood flowing through the second end of the graft portion toward the inferior end of the stent-graft portion will flow past the second end of the graft portion before flowing through the stent-graft portion.

In one form, the first end of the flexible graft portion is attached to the inferior end of the stent-graft portion and the junction is disposed at the inferior end of the stent-graft portion. In the pre-delivery configuration and the first delivered configuration, the flexible graft portion may extend inferiorly from the inferior end of the stent-graft portion, and in the second delivered configuration, the flexible graft portion extends superiorly from the inferior end of the stent-graft portion, and a first portion of the flexible graft portion is disposed within the stent-graft portion and a second portion of the stent-graft portion extends out of the stent-graft portion in a superior direction.

In another form, the junction is disposed at the superior end of the stent-graft portion and the flexible graft portion is disposed within the stent-graft portion in the pre-delivery configuration and the first delivered configuration.

In one approach, the system includes an aortic valve mounted to the mounting structure in the pre-delivery configuration, wherein, in the second delivered configuration, the aortic valve is disposed superior to the stent-graft portion, and when the aortic valve is in a compressed state, blood will flow through the mounting structure and past the aortic valve.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 5 is a schematic view of the prosthesis disposed within the vasculature in the first delivered configuration after the stent-graft portion has expanded radially into engagement with the patient's tissue, and prior to deployment of the graft portion, and further illustrating a balloon adjacent the dilator tip retracted into the valve that is mounted to the mounting frame;

FIG. 6 is a schematic view of the prosthesis disposed within the vasculature in the second delivered configuration, with the graft portion being deployed out of the stent-graft portion, and the valve expanded into engagement with the patient's tissue;

FIG. 7 is a schematic view of the stent-graft portion and the graft portion in the pre-delivery configuration and pre-loaded within a peel-away sheath, and the valve attached to the mounting frame of the graft portion at the inferior end of the stent-graft portion;

FIG. 10 is a view of the prosthesis in the first delivered configuration with the stent-graft portion in an expanded state into contact with the patient's tissue, with the graft portion still disposed within the stent-graft portion;

FIG. 11 is a view of the prosthesis with a delivery catheter retracted toward the operator and the balloon disposed within the valve;

FIG. 12 is a view of the prosthesis with the graft portion and valve moved superiorly relative to the stent-graft portion, along with the delivery catheter having the balloon, with the graft portion deployed out of the stent-graft portion, and the valve not yet fully expanded;

FIG. 12A is a view of the prosthesis in the second delivered configuration with the graft portion deployed out of the stent-graft portion and the valve in an expanded state;

FIG. 13 is a view of the prosthesis with branch extensions delivered;

FIG. 14 illustrates another embodiment of a prosthesis in a pre-delivery configuration, where a flexible graft portion is attached to and extends inferiorly from the inferior end of a stent-graft portion; and FIG. 15 illustrates the prosthesis of FIG. 14 in a deployed configuration, where the flexible graft portion has been everted, and a portion of the flexible graft portion is disposed within the stent-graft portion.

DETAILED DESCRIPTION OF THE PREFERRED EMBODIMENTS

In the present application, the term "superior" when referring to a delivery device refers to a direction that is farthest away from the operator using a delivery device, while the term "inferior" refers to a direction that is generally closest to the operator using the delivery device. The superior and inferior ends of a delivery device can also be referred to as the introduction end of the delivery device and the operator end of the delivery device. The operator end of the delivery device is that portion of the device that is intended to remain outside of a patient during a procedure. When referring to the prosthesis relative to placement in the human body, the ends of the various devices and parts of devices may be referred to as the inflow end (that end that receives fluid first), and the outflow end (that end from which the fluid exits). When referring to the prosthesis itself relative to the delivery device, with a retrograde or femoral artery delivery approach, the superior end of the prosthesis (the inflow end) is that part of the prosthesis nearest the delivery end of the delivery device and the inferior end of the prosthesis (the outflow end) is that end that is closest to the operator end of the delivery device. If an antegrade approach is used, the inferior (outflow) end is that part that is nearest the delivery end of the delivery device and the superior end is that closest to the operator).

The superior and inferior ends, openings, portions, or the like may also be referred to as superior and inferior, respectively. The superior designation can be used to refer to component or part of a component that is closer to the heart when delivered, while the inferior designation can be used to refer to a component or part of a component that is further from the heart. Similarly, reference to a superior direction can be used to refer to a direction toward the heart, and an inferior direction can be used to refer to a direction away from the heart. Superior or superiorly may be used in place of superior or superiorly. Inferior or inferiorly may be used in place of inferior or inferiorly.

Figure 1:
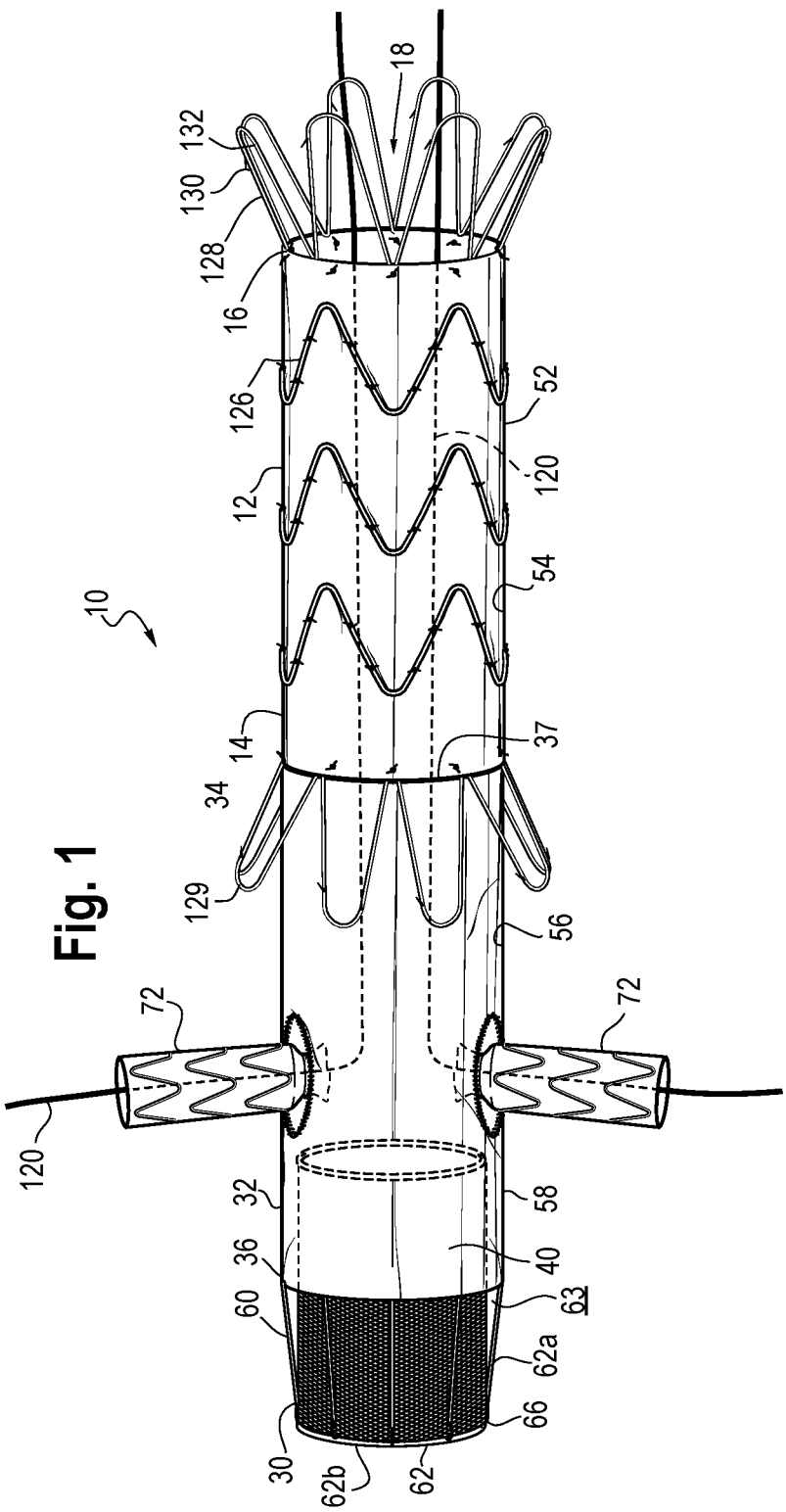
FIG. 1 is a side view of a prosthesis having a stent-graft portion and a flexible graft portion, illustrated in a second delivered configuration, with the graft portion outside and superior relative to the stent-graft portion.

FIG. 1 shows the prosthesis 10 in a delivered state. Prosthesis 10 includes a tube of graft material having a superior end for placement closest to the heart and an inferior end for placement furthest from the heart. From left to right, the prosthesis 10 includes a replacement heart valve (not shown in FIG. 1), a mounting frame 60 or other mounting structure configured to receive a replacement heart valve or other valve or medical device prior to delivery, graft portion 32 and stent stent-graft portion 12. In the delivered state, the valve 30 constitutes the superior most end of the prosthesis 10. In other words, once the prosthesis 10 is deployed fully in the body vessel, the valve is closest to the heart and is the inflow end of the device.

Further, referring to FIG. 1, the graft portion 32 has a superior end 36, an inferior end 34, and includes fenestrations or branches 72 between the superior and inferior ends that are configured to communicate with the coronary arteries of the ascending aorta for perfusion of blood to the coronary arteries. Extending inferiorly from the graft portion 32 is the stent-graft portion 12. Stent-graft 12 has a superior end 14 that corresponds to the inferior end 34 of the graft portion 32 (the graft portion/stent graft portion junction) and an inferior end 16 (the outflow end) of the prosthesis 10. An exposed stent 129 extends from the superior end 14 of the stent-graft portion 12 toward the superior end of the prosthesis 10. In the fully delivered state as shown in FIG. 1, the exposed stent 129 extends superiorly from the junction. An exposed stent 128 may also extend from the inferior end 16 of the stent graft 12.

One embodiment of the endoluminal prosthesis 10 includes the stent-graft 12 including a graft of a biocompatible material. The stent graft 12 can be generally tubular and includes a lumen 18 extending between the superior end 14 and the inferior end 16. Here, the superior end 14 is the end that when placed within the human body is the inflow end of the stent-graft 12, and the inferior end 16 is the outflow end of the stent-graft 12.

Many different types of graft materials may be used for the stent-graft 12. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues.

The endoluminal prosthesis 10 further comprises at least one stent coupled to the stent graft 12. As illustrated in FIG. 1, a plurality of stents 126 may be coupled to an outer surface of the stent graft 12 along the length thereof. However, the plurality of stents 126 can alternatively be coupled to an inner surface of the stent graft 12, or some of the plurality of stents 126 could be coupled to the inner surface while the other stents 126 are coupled to the outer surface. It will be appreciated the number of stents 126 and the coverage of the graft by the stents 126 can vary depending on the needs of the patient.

The stents 126 may be made from numerous metals, such as stainless steel, and alloys. In one example, the stents 126 comprise a shape-memory material such as a nickel-titanium alloy ("nitinol"). Moreover, the structure of the stents 126 may be formed in a variety of ways to provide a suitable intraluminal support structure. For example, one or more stents may be made from a woven wire structure, a laser-cut cannula, individual interconnected rings, or another pattern or design.

In the example of FIG. 1, the stents 126 may be configured in the form of one or more "Z-stents" or Gianturco stents, each of which may comprise a series of substantially straight segments interconnected by a series of bent segments. The bent segments may comprise acute bends or apices. The stents are arranged in a zigzag configuration in which the straight segments are set at angles relative to each other and are connected by the bent segments. However, as noted above, the stents 126 may comprise any suitable configuration and one or more stents may be provided.

The stent-graft 12 can be self-expandable, wherein the stent-graft 12 is compressed and radially retained in a compressed delivery state, and upon being released from the radial retention, the stent-graft 12 will expand due to, for example, a shape memory condition of the stents 126. Alternatively, the stents 126 can be biased toward an expanded condition, and upon deployment of the stent-graft 12, the stents 126 will expand the stent-graft 12 as the stents 126 expand.

In addition to the stents 126 that are disposed on the tubular sidewall of the stent graft 12, the stent graft 12 may further include the exposed stent 128 that is attached to the inferior end 16 of the stent graft 12 and the exposed stent 129 that is attached to the superior end 14 of the stent graft 12. The exposed stent 128 is disposed beyond the inferior end 16 of the stent graft 12 and includes free ends 130 defined by bends 132 of the exposed stent 128. When expanded, the free ends 130 may extend radially beyond an outer surface of the stent graft 12 to aid in anchoring the inferior end of the stent graft 12 to the patient's vasculature. Additionally, the stent graft 12 may include the exposed stent 129 at the superior end 14 that are arranged and constructed similarly to the exposed stent 128, with the free ends of the exposed stent 129 disposed superiorly relative to the superior end 14. In another approach, the stent graft 12 may include only the exposed stent 128 or only the exposed stent 129.

FIG. 1 illustrates the prosthesis 10 in a deployed state. However, the prosthesis 10 is designed to be folded over onto or into itself and delivered to the patient's vasculature in the folded state (FIG. 2), where the graft portion 32 is folded into the interior of the stent-graft portion 12. Upon delivery, the prosthesis 10 is configured to both expand and be unfolded in a manner further described below, such that it will ultimately be deployed into the arrangement shown in FIG. 1. By delivering the prosthesis 10 in a folded condition, the stent graft 12 of the prosthesis 10 can be deployed first, followed by the graft portion 32 and the remainder of the prosthesis 10, which can include other medical devices like a valve 30, such as an aortic valve, mounted thereto.

The above description of the stent graft 12 and its various related structure may be referred to as either the "stent-graft" or "stent-graft portion." The stent graft 12 is the portion of the prosthesis 10 that is disposed radially outward relative to the remainder of the prosthesis 10 in the pre-delivery configuration, where the graft portion 32 is folded into the stent graft 12, such that the stent graft 12 is the portion of the prosthesis 10 that is deployed or delivered to the vasculature "first." Of course, it will be appreciated that the delivery of the prosthesis 10 through the vasculature includes delivering the entire prosthesis, so reference to being deployed "first" refers to the order in which the graft portion becomes engaged with the vessel wall.

Figure 2:
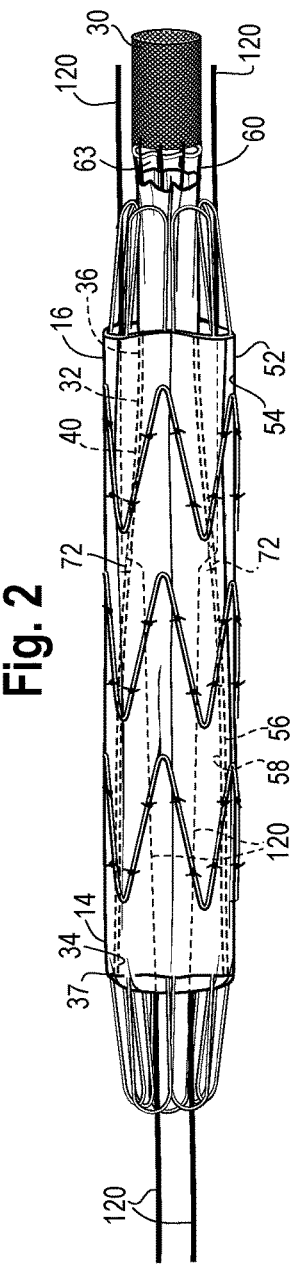
FIG. 2 is a side view of the prosthesis, illustrating the stent-graft portion and the graft portion in an infolded and radially compressed pre-delivery configuration, with the graft portion disposed within the stent-graft portion.

With reference to FIGS. 1 and 2, the prosthesis 10 further includes the flexible graft portion 32 that is attached to the stent graft 12. The graft portion 32 is the portion of the prosthesis 10 that is folded into the stent graft 12 when the prosthesis 10 is in the folded pre-delivery configuration shown in FIG. 2. The graft portion 32 may also be made of a graft material, similar to the stent-graft 12. The graft material used for the stent graft 12 and graft 32 may be a unitary piece of graft material, with the stent graft portion 12 being the portion that includes the stents 126, and the graft portion 32 being the portion that is without stents and the portion that is folded into the stent graft portion 12. For the sake of clarity, the graft portion 32 will described separately from the stent graft 12. Reference to the stent graft 12 will be considered a reference to the portion of the prosthesis 10 that includes the stents 126, and reference to the graft portion 32 will be considered a reference to the portion of the prosthesis 10 that is folded into the stent graft 12 during delivery and then transitioned out of the stent graft 12 into the state shown in FIG. 1.

As described above, the graft portion 32 has the inferior end 34 and the superior end 36 and includes a lumen extending therebetween. The inferior end 34 is attached to the superior end 14 of the stent graft 12, thereby coupling the flexible graft portion 32 to the stent graft 12. The graft portion 32 may have a flexible tubular sidewall 40 that defines the lumen.

The graft portion 32 can be made from the same material as the stent graft 12, such that it is attached to the stent graft 12 in a continuous manner. In another approach, the material of the graft portion 32 can be separate from the graft and fixed to the graft via stitching or other known retention methods that allow the graft portion 32 to pivot or bend relative to the stent graft 12.

The graft portion 32 is flexible such that it can be moved or rolled or unfolded longitudinally relative to the stent graft 12, with the inferior end 34 remaining attached to the superior end 14 of the stent graft 12. Movement of the graft portion 32 relative to the stent graft 12 can occur such that the tubular sidewall 40 will "roll" over itself, allowing it to be everted. Put another way, the superior end 36 of the flexible graft portion 32 moves toward the inflow or superior end 14 of the stent graft 12, and then moves beyond the superior end 14, such that the superior end 36 becomes the inflow end of the prosthesis 10 after being fully everted.

In one approach, the graft portion 32 may be free from stents or other support structure, allowing the graft portion 32 to be easily flexible relative to the stent graft 12. In another approach, the graft portion 32 may include some support structure, such as rings or stents, so long as such structure allows the graft portion to flex and bend or roll over itself as it is delivered out from the stent graft 12.

The movement or translation of the graft portion 32 relative to the stent graft 12 therefore provides multiple states or configurations of the prosthesis 10. As shown in FIG. 2, in the pre-delivery configuration, also referred to as a folded configuration, compressed configuration, pre-loaded configuration, or first configuration, the graft portion 32 is folded into the stent-graft portion 12, and the stent-graft portion 12 and graft portion 32 are radially compressed. In this configuration, the superior end 36 of the graft portion 32 is located at the inferior end 16 of the stent graft portion 12. This is the configuration shown in FIG. 2.

Figure 3:
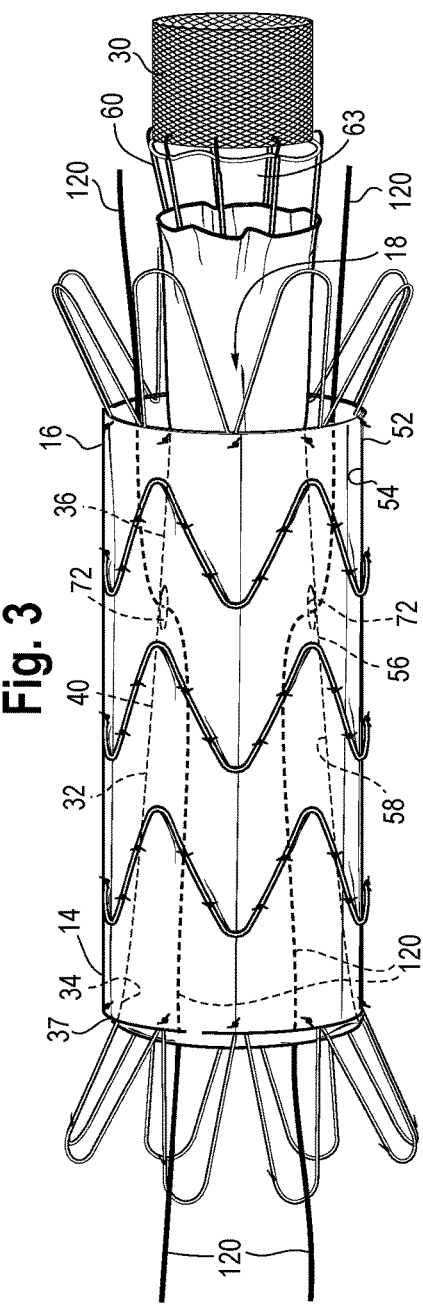
FIG. 3 is a side view of the prosthesis in a first delivered configuration, with the stent-graft portion radially expanded relative to the pre-delivery configuration.

As shown in FIG. 3, in the first delivered configuration, the stent-graft portion 12 is radially expanded, and the graft portion 32 is still disposed within the stent-graft portion 12, with the superior end 36 of the graft portion 32 located at the inferior end 16 of the stent graft portion 12. In this configuration, the graft portion 32 may still be radially compressed prior to being deployed out of the stent-graft portion.

In the second delivered configuration, such as that shown in FIG. 1, the graft portion 32 has moved superiorly relative to the stent-graft portion 12, and has been deployed out of the stent graft portion 12. The superior end 36 of the graft portion 32 is disposed superiorly from the junction between the graft portion 32 and the stent graft portion 12. The second delivered configuration can have two different states. In a first state, the superior end 36 is still radially compressed. In a second state, the superior end 36 is radially expanded along with the valve 30 mounted thereto. The second delivered configuration is shown in FIG. 1 in the second state. FIG. 12 shows the first state (after everting the graft portion 32, but before full expansion of the valve 30).

With reference again to FIG. 2, in the pre-delivery configuration, the inferior end 34 of the graft portion 32 is attached to the superior end 14 of the stent graft 12 and the superior end 36 of the graft portion 32 is disposed inferiorly from the inferior end 34 of the graft portion 32 and the superior end 14 of the stent graft 12. The inferior end 34 attaches to the superior end 14 of the graft at an interface 37 at the junction between the graft portion 32 and the stent graft portion 12. In this condition, the superior end 36 of the graft portion 12 may extend inferiorly beyond and out of the inferior end 16 of the stent graft 12, as shown in FIG. 3. In an alternative approach, the superior end 36 of the graft portion 32 may be aligned with the inferior end 16 of the stent graft portion, or the superior end 36 may be disposed slightly inboard from the inferior end 16. In each of these arrangements, the superior end 36 of the graft 32 may be described as being located at the inferior end 16 of the stent graft 12. Locating the superior end 36 of the graft 32 at the inferior end 16 of the stent graft portion in the pre-delivery configuration allows for the valve 30 to be attached to the prosthesis 10 when it is in its pre-delivery configuration and prior to loading the prosthesis 10 within the delivery device.

Thus, the graft portion 32 may have a length that is either shorter than the length of the stent graft 12 or longer than the length of the stent graft 12. The length of the graft portion 32 could also be the same as the stent graft 12. The relative length of the graft portion 32 relative to the stent graft 12 determines whether or not the superior end 36 terminates within the stent graft 12 or beyond the stent graft 12 when folded in the pre-delivery configuration.

Whether the superior end 36 is disposed within the graft lumen 18 or is disposed beyond the inferior end 16 of the stent graft 12, the tubular sidewall 40 of the graft portion 32 is disposed within the lumen 18 of the stent graft 12 and extends at least partially through the lumen 18 of the stent graft 12 in an inferior direction from the superior end 14 of the stent graft 12. When the superior end 36 is disposed beyond the end 16 of the stent graft 12, the tubular sidewall 40 will extend fully through the lumen 18.

In the second delivered configuration, as shown in FIG. 1, the inferior end 34 of the graft portion 32 is still attached to the superior end 14 of the graft, as in the pre-delivery configuration, because the graft portion 32 and the stent graft 12 remain attached after transitioning to the second delivered configuration. However, in the second delivered configuration, the tubular sidewall 40 is everted relative to the pre-delivery configuration, and the superior end 36 is disposed superior from the inferior end 34 of the graft portion and the superior end 14 of the graft.

As shown in FIG. 1, the tubular sidewall 40 is disposed outside of the graft lumen 18 when in the second delivered configuration, rather than inside the graft lumen 18 as in the pre-delivery configuration, and the tubular sidewall 40 extends superiorly away from the superior end 14 of the stent graft 12 and superiorly away from the interface 37 between the inferior end 34 of the graft portion 32 and the superior end 14 of the stent graft 12.

Thus, in the second delivered configuration, the stent graft 12 is arranged inferiorly relative to the graft portion 32, and the graft portion 32 is arranged superiorly from the stent graft 12. The superior end 36 is disposed at the superior end of the tubular sidewall 40, and the inferior end 34 is disposed at the inferior end of the tubular sidewall 40, and the tubular sidewall extends longitudinally between the inferior end 34 and the superior end 36. In this second delivered configuration, the prosthesis 10 therefore has the following arrangement in a direction from the inflow end to the outflow end beginning from the superior end 36 of the tubular sidewall 40. The superior end 36 of the tubular sidewall 40 transitions to the tubular sidewall 40, which transitions to the inferior end 34 of the tubular sidewall 40, which is attached to the superior end 14 of the stent graft 12, which transitions to the body of the stent graft 12, which transitions to the inferior end 16 of the stent graft 12.

Accordingly, the second delivered configuration defines an elongated arrangement that combines the graft portion 32 and the stent graft 12. The pre-delivery configuration defines a longitudinally shortened and folded arrangement, where the graft portion 32 is folded into the interior of the stent graft 12, with the fold occurring generally at the interface 37 between the graft portion 32 and the stent graft 12.

The stent graft 12 and the graft portion 32 both have generally tubular shapes, and therefore each include surfaces on opposite sides of their tubular bodies. The stent graft 12 has an arrangement remaining generally the same between the pre-delivery configuration and the second delivered configuration of the graft portion 32. Thus, the stent graft 12 includes an outer surface 52 and an inner surface 54.

As described above, the graft portion 32 is flexible and can be everted between the pre-delivery configuration and the second delivered configuration. Thus, the graft portion includes a first surface 56 and a second surface 58. However, whether either the first surface 56 or the second surface 58 is inwardly facing or outwardly facing depends on the state or configuration of the graft portion 32.

In the pre-delivery configuration shown in FIG. 2, with the graft portion 32 disposed generally within the stent graft 12, the first surface 56 faces outwardly, with the first surface 56 facing the inner surface 54 of the stent graft 12 or contacting the inner surface 54 of the graft. In this pre-delivery configuration, the second surface 58 faces inwardly and defines a lumen through the graft portion 32.

In the second delivered configuration shown in FIG. 1, with the graft portion 32 having been everted and extending superiorly away from the stent graft 12 and outside of the lumen 18 of the stent graft 12, the first surface 56 faces inwardly and defines the lumen 38 through the graft portion 32. The first surface 56, in this configuration, transitions to the inner surface 54 of the stent graft 12 at the interface 37, such that the first surface 56 and inner surface 54 combine to define a longitudinal lumen fully through the prosthesis 10. The second surface 58, in this configuration, faces outwardly, and transitions to the outer surface 52 of the stent graft 12, such that the second surface 58 and the outer surface 52 combine to define the outward facing structure of prosthesis 10.

The different configurations of the graft portion 32 allow various structure attached to the graft portion 32 to be in different positions depending on the configuration. The pre-delivery configuration of FIG. 2 can also be a delivery configuration (where the prosthesis 10 can be loaded into a delivery sheath), and can be a preloaded configuration of the prosthesis 10 when the prosthesis 10 is disposed within a delivery device. The second delivered configuration of FIG. 1 is preferably the ultimate delivered configuration, and is the configuration in place when the prosthesis 10 is left in the patient's body. The first delivered configuration of FIG. 3 is an intermediate configuration that exists between the pre-delivery configuration and the second delivered configuration, where the stent-graft portion 12 is expanded, but the graft portion 32 is still inside the stent-graft portion 12.

With reference to FIGS. 1 and 3, the graft portion 32 includes the mounting frame 60 disposed at the superior end 36. Thus, the mounting frame 60 will move relative to the stent graft 12 when the mounting frame 60 transitions from the first delivered configuration to the second delivered configuration along with the graft portion 32 after the prosthesis 10 has been introduced into the body. The mounting frame 60 is configured such that a valve 30, such as an aortic valve, can be mounted thereto. Advantageously, the valve 30 may be mounted to the prosthesis 10 when it is in the pre-delivery configuration, such that it can be delivered to the patient's body already attached, and without the need to first deliver the valve 30 prior to the prosthesis, or the need to deliver the valve 30 after the prosthesis 10 has been delivered.

In one approach, as shown in FIG. 1, the mounting frame 60 is in the form of a frame such as a wire frame 62 including struts 62*a* and a ring 62*b*. The struts 62*a* may support the ring 62*b*, which together are configured to support the valve 30 having a corresponding mounting structure. In another approach, the wire frame 62 may exclude the ring 62*b*. The ring 62*b* is preferably flexible in nature, such that it can expand along with the expansion of the aortic valve 30 after it has been deployed at the target location.

In this form, the mounting frame 60 having a wire frame 62 thereby defines a plurality of openings 63 through the frame 62, which allows blood to flow through the mounting frame 60 for perfusion. Accordingly, with the mounting frame 60 disposed on the superior end 36 of the graft portion 32, blood will not be blocked when the device is delivered in the first delivered configuration, and blood can flow through mounting frame 60 and the graft portion 32 while it is within the stent graft 12 before the prosthesis 10 has transitioned from the first delivered configuration to the second delivered configuration. Once the attached valve 30 has been deployed and expanded to its ultimate position, blood can flow through the valve 30 as part of its normal operation, and the openings 63 of the mounting frame may be blocked. Similarly, after the graft portion 32 has been everted but before full expansion of the valve 30, blood may flow through the mounting frame 60 and through the prosthesis 10.

In one approach, the mounting frame 60 includes hooks 66 disposed on the frame 62 that can be crimped to corresponding structure on the valve 30 that is being attached to the mounting frame 60. Other approaches to connecting a valve 30 to a mounting frame could also be used.

With the mounting frame 60 disposed on the superior end of the graft portion 32, the mounting frame 60 is thereby disposed near the inferior end 16 of the prosthesis 10 when the prosthesis 10 is in the pre-delivery configuration shown in FIG. 2. The prosthesis 10 is typical delivered with the superior end 14 first. In the arrangement of FIG. 2, the end 36 of the graft portion 32 being adjacent the inferior end 16 of the stent graft 12 allows the end 36 of the graft portion to be easily accessed by the operator to attach the valve 30 even when the prosthesis 10 is in a preloaded compressed state or pre-delivery condition. Thus, the mounting frame 60 can be exposed to users of the system for later installation of the valve 30 without affecting the pre-loaded nature of the prosthesis 10. Transitioning the graft portion 32 from the first delivered configuration to the second delivered configuration will thereby also transition the mounting frame 60, and the valve 30 mounted thereto, to the opposite end (the inflow end) of the prosthesis 10 when deployed.

By attaching the valve 30 to the prosthesis 10 in a folded pre-delivery configuration, the stent-graft portion 12 of the prosthesis 10 along with its tissue engagement features can be delivered first, with the deployment of the graft portion 32 and the valve 30 occurring after the stent graft 12 has been deployed. Thus, a single delivery system can be used to deliver both the stent graft 12 and the valve 30. This is advantageous relative to deploying the valve 30 separately or after deploying a separate graft, because deploying them separately adds time and complexity to the process, and could require multiple attempts.

With reference again to FIG. 1, the graft portion 32 of the prosthesis 10 can also include one or more ports or fenestrations or passageways 72 through the tubular sidewall 40 to allow for blood flow to adjacent blood vessels. The passageways 72 can be in the form of fenestrations or branches or the like and can receive a branch extension prosthesis 72a (as shown in FIG. 1) that may be used to provide blood flow into a branch vessel. The passageway 72 provides fluid communication from one side of the tubular sidewall 40 to the other, such that blood flowing through the interior of the graft portion 32 can flow through the passageway 72 to the exterior of the graft portion 32 or to additional branch extension prostheses. The passageway 72 in the form of a branch can be straight, curved, helical, pivoting, or other known branch or tubular fenestration styles. Alternatively, the passageway 72 could be in the form of through-hole in the tubular sidewall 40, as shown in FIGS. 2-6.

The passageways 72 are preferably arranged on the tubular sidewall 40 such that they will be disposed near the blood vessels where cannulation and blood flow is desired. In one approach, the passageways 72 are arranged to provide blood flow from within the graft portion 32 disposed in the ascending aorta to the coronary arteries. The passageways 72 are disposed through the sidewall 40 at a longitudinal location between the first end 34 of the graft portion 32 and the second end 36 of the graft portion. In the pre-delivery condition and first delivered configuration, as shown in FIGS. 2 and 3, the passageways 72 are disposed inferiorly from the inferior end 34 and superiorly from the superior end 36. In the second deployed condition, shown in FIG. 1, the passageways 72 are disposed superiorly from the inferior end 34 and inferiorly from the superior end 36.

Due to the nature of the graft portion 32 being everted or flipped when transitioning from the first condition to the second condition, the passageways 72 of a branch form are preferably arranged such that the end that is initially extending inwardly from the graft portion 32 in the first delivered configuration is the end that will extend outwardly after transitioning to the second delivered configuration of FIG. 1. Thus, in the case of a branch that is intended to extend outwardly when ultimately deployed, the end that extends outwardly when deployed in the second delivered configuration would extend inwardly in the first delivered configuration.

For the sake of discussion, a first end of the branch 72 is the end that is disposed inwardly from the tubular sidewall 40 in the first delivered configuration and the pre-delivery configuration and the end that is disposed outwardly from the tubular sidewall 40 in the second delivered configuration. A second end may be attached to the tubular sidewall, or it may be disposed away from the tubular sidewall 40 on the side opposite the first end. The branches 72 can be catheterized either before or after the prosthesis 10 is delivered to the patient, depending on the patient's anatomy.

The prosthesis 10 is preferably delivered to the target site via the use of an introducer 100 (FIG. 4) in a manner known in the art. The introducer 100 includes an outer sheath 102 and a dilator tip 104, and a delivery catheter 106. An introducer, such as that described in PCT application WO98/53761, entitled "A Prosthesis and a Method and Means of Deploying a Prosthesis," which is incorporated herein by reference in its entirety, may be used to deploy the stent graft 12. PCT application WO98/53761 describes a deployment system for an endoluminal prosthesis whereby the prosthesis is radially compressed onto a delivery catheter and is covered by an outer sheath.

To deploy the system, the operator slides or retracts the outer sheath 102 over the delivery catheter 106 toward the operator end, thereby exposing the prosthesis 10 including the stent graft 12 with the graft portion 32 being disposed inside the stent graft 12. The stent graft 12 expands outwardly upon removal of the sheath 102. Expansion of the stent graft 12 can occur via self-expansion, or it can alternatively occur via inflation of a balloon 107 of the catheter 106. The operator can directly manipulate the sheath 102 and the delivery catheter 106, which provides the operator with a relatively high degree of control during the procedure. Further, such delivery devices and introducers 100 may be compact and may have a relatively uniform, low-diameter radial profile, allowing for atraumatic access and delivery.

With reference to FIG. 5, once the stent graft 12 has been exposed from the sheath 102 and has been radially expanded and deployed into engagement with the blood vessel, the delivery catheter 106 and balloon 107 can be retracted toward the operator into the valve 30 for coupling with the valve 30, and the balloon 107 can be inflated to partially expand the valve 30, if necessary. Once the stent graft 12 has been expanded and the valve 30 is prepared for deployment, the flexible graft portion 32 and the valve can be pushed out and deployed from within the stent graft 12.

After the stent graft 12 has been deployed, blood entering the superior end 14 (inflow end) of the stent graft 12 will flow into the interior of the graft portion 32. As described above, the mounting frame 60 includes openings 63 therethrough, such that blood flow can continue through the prosthesis 10 without being substantially blocked. Accordingly, blood flow can be maintained prior to the valve 30 being fully deployed and functional.

With reference to FIG. 6, a pusher member 108 can be included that cooperates with the catheter 106 and balloon 107 to move the superior end 36 of the graft portion 32 and valve 30 superiorly relative to the inferior end 34, which remains attached to the superior end 14 of the stent graft 12. The superior end 36 of the graft portion 32 is ultimately positioned at a superior end of the graft portion 32 and at the location where the valve 30 is desired. The valve 30 is thereby located at the desired position according to its connection to the mounting frame 60 that is disposed on the superior end 36 of the graft portion.

As shown in FIGS. 5 and 6, and with further reference to the balloon 107 of the delivery catheter 106, the balloon 107 can be retracted and positioned within the valve 30 and expanded/inflated to partially expand the valve 30, if desired. In one approach, the balloon 107 is disposed adjacent the dilator tip 104, which is connected to the delivery catheter 106. The delivery catheter 106 can be retracted toward a stop member 112 of the pusher member 108, such that the balloon 107 will be positioned within the valve 30 in accordance with the location of the stop member 112. Thus, the catheter 106 can be coupled to the pusher member 108 via the stop member 112, and the catheter 106 can likewise be coupled to the valve 30. After coupling the valve 30 to the catheter 106, the pusher member 108 can be advanced to move the catheter 106, valve 30, and catheter 106/balloon 107 superiorly to transition the prosthesis 10 from the first delivered configuration (FIG. 5) to the second delivered configuration (FIG. 6).

In another approach, the pusher member 108 can be excluded, and the transition from the first delivered configuration to the second delivered configuration can be performed by engaging the catheter 106 with the valve 30 or the superior end 36 of the graft portion 32, and thereafter moving the catheter 106 in the insertion direction away from the operator. Proper positioning of the balloon 107 such that the catheter 106 will engage the valve 30 can be accomplished via known monitoring methods, such as through the use of radiopaque markers on the components. It will be appreciated that other methods of engaging and transitioning the graft portion 32 from the first delivered configuration to the second delivered configuration can also be used.

With the prosthesis 10 in the second delivered configuration (but without final expansion of the valve), the valve 30 is also positioned in the second delivered configuration and disposed at the desired location. The balloon 107 preferably remains within the valve 30 or can be adjusted to be within the valve 30. With the valve 30 in the desired location, and the balloon 107 disposed within the valve 30, the balloon 107 can be inflated to expand the valve 30 into engagement with the surrounding tissue, as shown in FIG. 6. While the expansion of the valve 30 has been described as occurring in response to inflation of the balloon 107, the valve 30 may also be self-expandable without the use of a balloon.

Once the valve 30 and prosthesis 10 have been expanded and ultimately deployed in the desired position within the vasculature, the delivery catheter 106 and the remaining components of the introducer 100 can be retracted and removed from the patient, leaving the prosthesis 10 and valve 30 in place.

Additionally, and with reference again to FIGS. 1-4, the system can include one or more preloaded wires 120 along with the prosthesis 10 that extend through the passageways 72 of the graft portion 32. In the folded pre-delivery configuration shown in FIG. 2, the wires 120 extend in the inferior to superior direction, entering the lumen 18 of the stent graft 12 and passing by the superior end 36 of the graft portion 32 while being disposed radially between the stent graft 12 and the graft portion 32. The wires 120 further extend through the passageways 72 into the interior of the graft portion 32, and further out of the inferior end 34 of the graft portion and the superior end 14 of the stent graft 12. The wires 120 may also terminate prior to reaching the superior end 14 of the stent graft 12 when the stent graft 12 is in the preloaded pre-delivery configuration.

Upon exposure of the prosthesis from the introducer 100 during delivery, the wires 120 can be extended out of the superior end 14 of the stent graft 12 and can be extended into desired blood vessels prior to deploying the graft portion 32 and unfolding the prosthesis 10. When the graft portion 32 moves from the first delivered configuration to the second delivered configuration, the passageways 72 will slide along the wires 120 and will ultimately be disposed at the location of the blood vessels where the wires 120 extend.

In the second delivered configuration, the wires 120 will still extend through the inferior end of the stent graft 12, but the movement of the graft portion 32 results in the wires 120 extending from the inferior end of the stent graft 12 and through the interior of the graft portion 32, and then extending through the passageway 72 to the exterior of the graft portion 32, as shown in FIG. 1

With the passageways 72 and wires 120 disposed adjacent the desired blood vessels, additional branch extensions can be introduced over the wires 120 and the vessels can be catheterized in a manner known in the art. Thereafter, the wires 120 can be retracted out of the patient.

In the above description, the mounting frame 60 of the graft portion has been described as being configured to attach to a valve 30. In one approach, the valve 30 is in the form of an aortic valve 130 that can replace damaged aortic valves due to aortic valve stenosis or other undesirable conditions of a patient's aortic valve. Aortic valves used in aortic valve replacement are well known in the art. Aortic valves can be of the type that are balloon-expandable to replace a malfunctioning valve. When used with the above described system, the prosthesis 10 can be delivered to a location above the malfunctioning aortic valve in the ascending aorta, with the aortic valve 130 being disposed adjacent the malfunctioning aortic valve when the prosthesis 10 is unfolded and deployed in the second delivered configuration. The aortic valve 130 is expanded via the balloon 107.

As described above, the superior end 36 of the graft portion 32 can be disposed inferiorly from the inferior end 16 of the stent graft 12 when the prosthesis 10 is in the pre-delivery condition, or the superior end 36 having the mounting frame 60 can be disposed near or adjacent the inferior end 16 of the graft portion 12 of the prosthesis 10. Alternatively, the superior end 36 can be disposed superiorly from the inferior end 16, such that it terminates within the lumen 18 of the stent-graft portion 12, so long as the mounting frame 60 may still be accessed by the operator to attach the valve 130.

With reference to FIG. 7, a peel-away sheath 150 can be provided over the stent-graft portion 12 and the superior end 36 of the graft portion 32 when it is in the folded pre-delivery condition. Thus, the prosthesis 10 can be pre-loaded and compressed into the pre-delivery condition, where the valve 30 can be added to the prosthesis 10 at a later time. The peel-away sheath 150 can be removed to expose the mounting frame 60 that is located at the superior end 36 of the graft portion, or the mounting frame 60 may be exposed prior to peeling away the sheath 150. As shown in FIG. 7, the mounting frame 60 is exposed prior to peeling away the sheath 150. The remainder of the prosthesis 10 can remain loaded within the peel-away sheath 150 and remain covered.

This arrangement allows for the valve 30 to be attached to the exposed mounting frame without affecting the pre-loaded nature of the prosthesis 10. Thus, the valve 30 can be "after-loaded" to the prosthesis 10 that has been preloaded in the sheath 150. This after-loading allows for easy installation of a desired valve 30 that fits the specific needs of the patient.

The pre-loaded prosthesis 10, after attaching the valve 30 thereto, can be loaded into the introducer 100 in a manner known in the art, with the peel-away sheath being peeled away as the prosthesis 10 and valve 30 are loaded into the introducer 100. Alternatively, the prosthesis 10 may be loaded into the introducer 100 prior to attaching the valve 30, with the mounting frame 60 remaining exposed to the physician, and the valve 30 may be attached to the exposed mounting frame 60, and then loaded further into the introducer 100.

Moreover, the pre-loaded and folded pre-delivery configuration of the prosthesis 10 results in the delivery of the prosthesis 10 such that the stent graft 12 is delivered and deployed first, followed by the graft portion 32 and valve 30 being deployed thereafter. Effectively, the portion of the prosthesis 10 that is the inferior portion when ultimately deployed is deployed prior to the portion that is the superior portion when ultimately deployed utilizing a single delivery system.

Having described the structure and function of the prosthesis 10 and its components, a method for deploying the prosthesis 10 will now be described with reference to the delivery and deployment steps.

The prosthesis 10 having the stent graft 12 and the graft portion 32 disposed within the stent graft 12 in the pre-delivery configuration is provided in a preloaded state. The valve 30 may then be attached to the mounting frame 60 that is disposed at the second end 36 of the graft portion 32. If the peel-away sheath 150 is used to cover the mounting frame 60, the peel-away sheath can be removed prior to attaching the valve 30, and can be further removed while attaching the prosthesis 10 and valve 30 to the introducer.

Figure 4:
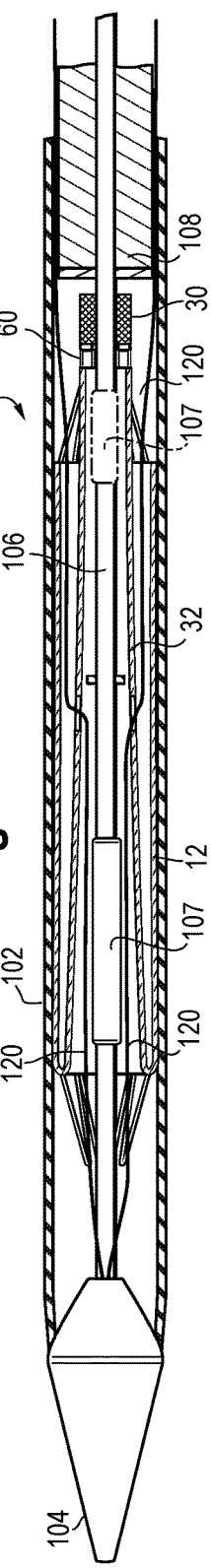
FIG. 4 is a schematic side view of the prosthesis in the pre-delivery configuration and disposed within a delivery system.

With reference to FIG. 4, the prosthesis and valve are loaded into to the introducer 100. More particularly, the prosthesis 10 is housed within the delivery sheath 102, with the superior end of the stent graft 12 portion and the inferior end 34 of the graft portion 32 disposed adjacent the dilator tip 104, and the superior end 36 of the graft portion 32 is disposed at the opposite end from the dilator tip 104.

With reference to FIGS. 8-13, the introducer 100, including the dilator tip 104 and the delivery sheath 102 are introduced into the patient's vasculature in a percutaneous manner and away from the user. The dilator tip 104 and delivery sheath 102 are advanced into the desired blood vessel, for instance the ascending aorta. The stent graft 12, being disposed within the delivery sheath 102, is thereby delivered to the desired location within the blood vessel. The position of the dilator tip 104 and the delivery sheath 102 can be monitored using known monitoring methods to position the stent graft 12 in the desired location.

Figure 9:
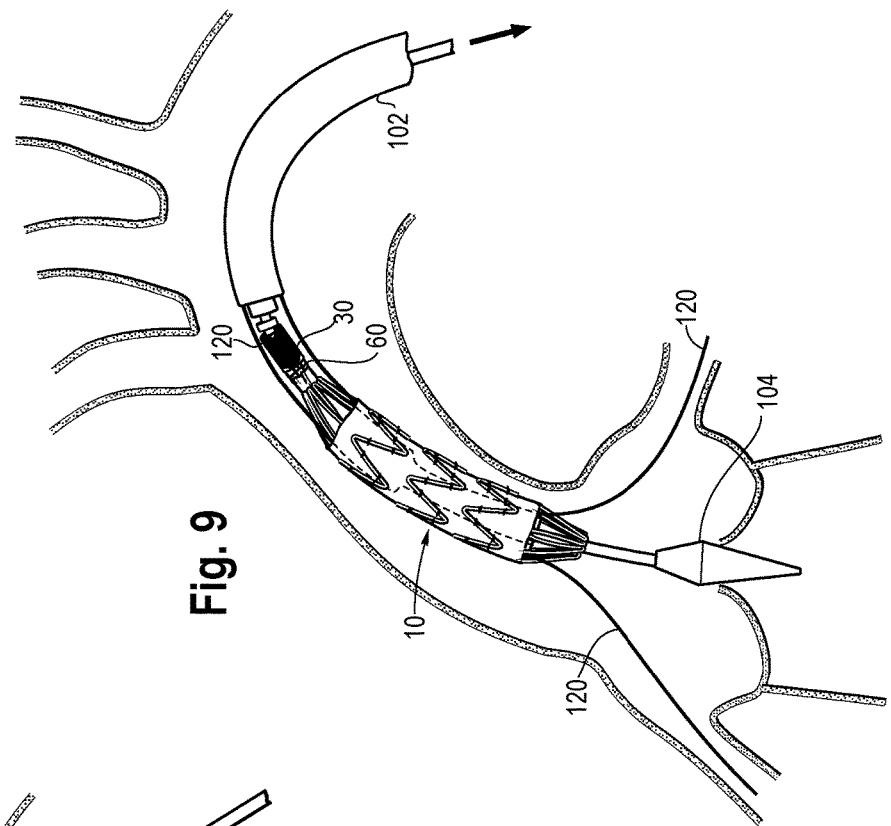
FIG. 9 is a view of the prosthesis exposed from the delivery sheath and prior to expansion of the stent-graft portion.
Figure 8:
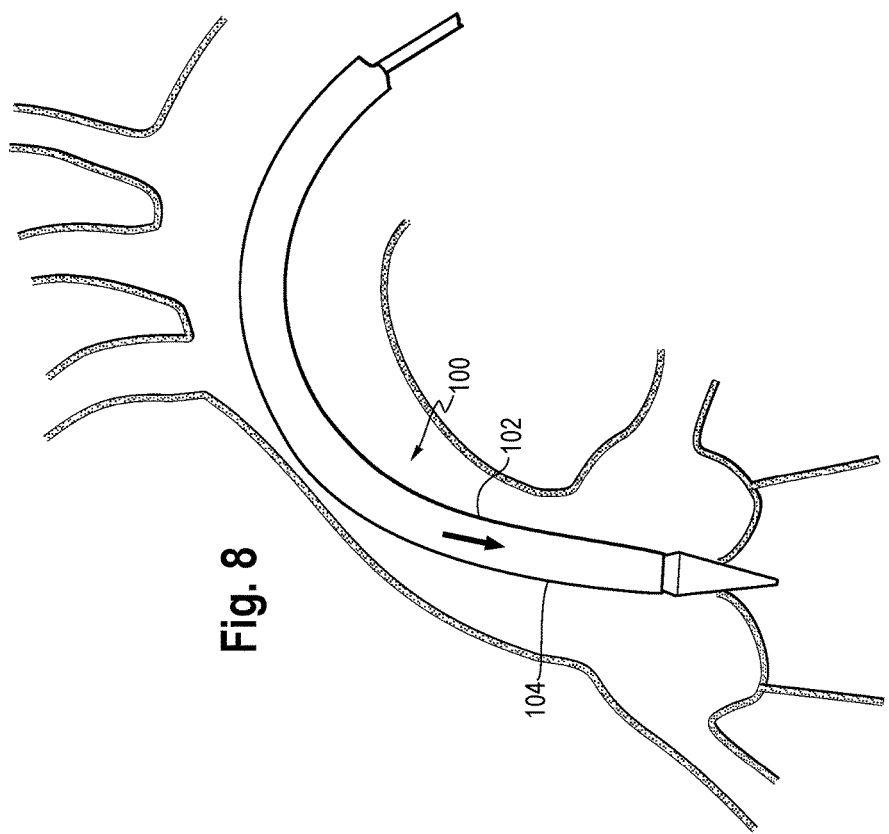
FIG. 8 is a view of the delivery of the prosthesis, showing an introducer with a dilator tip and delivery sheath introduced into the patient.

As shown in FIG. 9, upon reaching the desired location for graft deployment, the delivery sheath 102 is retracted toward the user and away from the dilator tip 104. In response to retracting the delivery sheath 102, the stent graft 12 is exposed and can expand radially outward into engagement with the vessel wall, as shown in FIG. 10. The expansion of the stent-graft portion 12 results in the prosthesis being in the first delivered configuration. This expansion can occur due to self-expansion of the stent graft 12, or alternatively via the use of the balloon 107 if necessary. The exposed stents 128 and 129 of the stent graft 12 are also exposed from the delivery sheath 102 and will engage the vessel wall. Thus, the stent graft 12 will be securely located within the blood vessel as shown in FIGS. 10-13.

If the prosthesis 10 includes the pre-loaded wires 120 extending through the prosthesis 10 and through the passageways 72 of the graft portion 32, the wires 120 can be moved away from the operator and toward the insertion end, as shown in FIGS. 9 and 10. The wires 120 can be routed into a desired branch vessel (FIGS. 10-13) to assist in later delivery of branch extension prostheses into the branch vessels.

With the prosthesis 10 being in the first delivered configuration (FIGS. 10 and 11), the prosthesis 10 can then transition to the second delivered configuration shown in FIGS. 12 and 13. The balloon 107 may be retracted such that it is aligned with the location of the aortic valve 30 to partially expand the valve 30 and engage with the valve to assist pushing the valve 30 and the flexible graft portion 32 in the superior direction. The graft portion 32 is pushed superiorly and transitioned from the folded first delivered configuration to the longitudinally extended second delivered configuration, being everted in the process, as shown in FIGS. 12 and 13. The superior end 36 of the graft portion 32 is moved superiorly relative to the stent graft 12, taking the valve 30 mounted thereto along with it and likewise moving the valve 30 superiorly relative to the stent graft 12. The inferior end 34 of the graft portion 32 remains attached to the superior end 14 of the stent graft 12. The valve 30 is thereby translated superiorly and disposed at the desired location for deployment.

In transitioning the graft portion 32 to the second delivered configuration, the various orientations and arrangements of the structure corresponding to the graft portion 32 will also transition from their orientation and arrangement in the first delivered configuration to their orientation and arrangement in the second delivered configuration as described above. For example, the first and second surfaces 56 and 58 of the graft portion 32 will go from being inwardly facing to being outwardly facing, or outwardly facing to being inwardly facing. These relative arrangements are shown in FIGS. 1 and 2.

As the graft portion 32 is being unfolded and moved superiorly relative to the stent graft 12, the passageways 72 of the graft portion will slide over the wires 120, such that the wires 120 remain in place and extending into the adjacent branch vessels.

In one approach, to translate the valve 30 superiorly relative to the graft and evert the graft portion 32, the delivery catheter 106 and dilator tip 104 can be retracted toward the user and inferiorly toward the valve 30 to engage and couple to the valve 30, as shown in FIG. 11. Then, the delivery catheter 106, being coupled to the valve 30, can be pushed away from the user and superiorly relative to the stent graft 12, as shown in FIG. 12, moving the valve 30 toward the desired deployment location and everting the graft portion 32. In the position illustrated in FIG. 12, the valve 30 is not fully expanded, and in this configuration blood can flow through the mounting frame 60 and around the valve 30

In another approach, the pusher member 108 can be advanced away from the user to push the valve 30 superiorly relative to the stent graft 12 and everting the graft portion 32.

As shown in FIG. 12A, with the valve 30 positioned as desired, the balloon 107 can be inflated to expand the valve 30 into engagement with the patient's tissue. The balloon 107 can be moved into the valve 30 by retracting the delivery catheter 106, or the valve 30 can be pushed over the balloon 107 that is disposed at the deployment location. In another approach, the valve 30 can include a preloaded balloon therein that moves with the valve 30.

The delivery sheath 102, delivery catheter 106, and dilator tip 104 can be retracted after the valve 30 has been positioned at the desired location and expanded as shown in FIG. 12A.

As shown in FIG. 13, after everting the graft portion 32 and expanding the valve 30, branch extension prostheses 72a can be delivered over the wires 120 and into engagement with the passageways 72 to provide a blood flow path into corresponding branch blood vessels. The wires 120 can then be retracted after the branch extension prostheses 72a are deployed.

As described above and shown in FIG. 10, the wires 120 can be extended into the branch vessels prior to everting the graft portion 32. In an alternative approach, the wires 120 are routed into the branch vessels after everting the graft portion 32. Preferably, the wires are extended into the branch vessels prior to everting the graft portion 32 to limit instances where the graft portion 32 translates superiorly and the passageways 72 move beyond the ends the of the wires, requiring re-routing of the wires through the passageways 72. However, routing of the wires 120 through the passageways 72 after deployment of the graft portion 32 can be done in the event the passageways 72 and wires 120 become disengaged.

Delivery of the branch extension prostheses 72a can occur before or after removal of the delivery sheath and delivery catheter, depending on the needs of the user.

Upon deployment of the prosthesis 10 as described above, the valve 30 will be deployed at the desired location and attached to the prosthesis 10 via the mounting frame 60 and also in engagement with the graft material of the graft portion 32. Blood will be allowed to flow through the valve 30, the graft portion 32, and the stent graft 12, as well as into branch vessels via the passageways 72 and branch extension prostheses. Thus, bloodflow will be maintained within the patient after deployment of the prosthesis 10 and valve 30.

The above described prosthesis 10 has been described as having a stent-graft portion 24 and a flexible graft portion 32, where when deployed and everted the inferior end of the flexible graft portion 32 is attached to the superior end 14 of the stent-graft portion 12 at the junction 37 therebetween. In an alternative approach, as shown in FIGS. 14 and 15, a prosthesis 210 may be used where, when deployed as shown in FIG. 15, an inferior or first end 234 of a flexible graft portion 232 is attached to an inferior end 216 of stent-graft portion 212, and the superior or second end 236 of the flexible graft portion 232 is disposed superiorly from a superior end 214 of the stent-graft portion 212.

FIG. 14 illustrates the prosthesis 210 in a pre-delivery configuration, but is shown expanded for illustrative purposes. In the pre-delivery configuration, the prosthesis 210 would be compressed.

In this approach, the flexible graft portion 232 is substantially longer than the stent-graft portion 212. Similar to the above, the ends of the stent-graft portion 212 and 232 flexible graft portion are described with reference to their positions when fully deployed within the body vessel. In the pre-delivery configuration, illustrated in FIG. 14, the orientation of the flexible graft portion 232 is opposite its orientation of the fully deployed configuration.

Thus, the inferior end 234 of the flexible graft portion 232 is attached to the inferior end 216 of the stent-graft portion 212 at a junction 237, and remains attached throughout the delivery and deployment of the prosthesis 110. In the pre-delivery configuration, the first end 234 of the flexible graft portion 232 is disposed superiorly from the second end 236 of the flexible graft portion 232, and after delivery and being everted, the first end 234 will be disposed inferiorly from the second end 236.

As described above, the flexible graft portion 232 is longer than the stent-graft portion 212 in this approach. The flexible graft 232 is made longer, such that after it is everted as shown in FIG. 15, a first portion 232a of the flexible graft portion 232 is disposed within the lumen of the stent-graft portion 212, and a second portion 232b extends superiorly from the first portion 232a that is within the stent-graft portion 212. The portion 232a of the flexible graft portion 232 that is disposed within the stent-graft 212 after being everted may also be referred to as the inferior section, and the second portion 232b that extends superiorly away from the stent-graft portion 212 and the inferior section 232a of the flexible graft portion 232 may be referred to as the superior section. The terms "superior" and "inferior" used for these sections of the flexible graft portion correspond to their position and orientation after being delivered and everted. Thus, in the pre-delivery configuration and prior to being everted, the superior section 232b is closer to the operator than the inferior section 232a.

The superior section 232b of the flexible graft portion 232 can include the same structure described above that relates to the flexible graft portion 32. The difference between the superior section 232b of the flexible graft portion 232 and the previously described flexible graft portion 32 is that the superior section 232b is not directly attached to the superior end 214 of the stent-graft portion 212. Rather, the superior section 232b of the flexible graft portion 232 is attached to the stent-graft portion 212 via the inferior section 232a. The superior section 232b transitions to the inferior section 232a, which extends toward the stent-graft portion 212 and attaches to the stent-graft portion 212 at the junction 237.

In this approach, once the flexible graft portion 232 has been delivered and everted, the combination of the superior section 232b of the flexible graft portion 132 and the stent-graft portion 212 will resemble the previously described combination of the flexible graft portion 32 and the stent-graft portion 12. The difference between these embodiments is that the superior section 232b does not join with the stent-graft portion 212 at the superior end 214 of the stent-graft portion 214. Rather, the superior section 232b transitions into the inferior section 232a. The inferior section 232a is disposed within the stent-graft portion 212 and extends inferiorly to the inferior end 216 of the stent-graft portion 212, where the inferior section 232a joins with the inferior end 216 of the stent-graft portion 212 at the junction 237.

In the pre-delivery state, the flexible graft portion 232 is not folded into the stent-graft portion 212. Rather, the stent-graft portion 212, inferior section 232a of the flexible graft portion 232, and superior section 232b of the flexible graft portion 212 are arranged longitudinally adjacent each other in that order in a direction from the insertion end toward the operator end.

The mounting frame 60 described previously above is used in this embodiment in the same manner. The mounting frame 60 is attached to the superior end 236 of the superior section 232b, similar to how it is attached to the superior end 36 of the flexible graft portion 32 of the previously described embodiment, and a valve 30 may be attached to the mounting structure in the pre-delivery configuration.

The superior section 232b may further include the previously described passageways 72, such that when the flexible graft portion 232 is everted as shown in FIG. 15, the passageways 72 will be disposed superiorly from the superior end 214 of the stent-graft portion 212. The previously described wires 120 that may be pre-loaded in the pre-delivery configuration or prior to delivery into the patient may also be used. Similar to the above description related to the wires 120, the wires 120 enter the interior of the flexible graft portion 232 through the passageways 72 and then continue through the prosthesis 210 and exit through the superior end 214 of the stent-graft portion. Unlike the previous embodiment, the wires 120 do not need to be disposed radially between the graft portion 232 and the stent-graft portion 212, because the wires 120 enter the interior of the graft portion 232 at a location outside of the stent-graft portion 212.

In the pre-delivery configuration, the passageways 72 are not located within the stent-graft 212 as they are in the previous embodiment. Rather, the passageways 72 are located inferiorly from the stent-graft portion 232. Thus, the wires 120 may extend into the superior section 232b through the passageways 232, and then extend superiorly within the superior section 232b and through the inferior section 232a, and further through the stent-graft portion 212. The wires may be advanced into the desired branch vessels prior to everting the flexible graft portion 232, and the passageways 72 will slide along the wires as the flexible graft portion 232 is everted, such that the passageways 72 will ultimately be disposed superiorly from the superior end 214 of the stent-graft portion 212 and near the desired branch vessels.

The flexible graft portion 232 and the stent-graft portion 212 may be loaded into a similarly arranged peel away sheath (not shown for this embodiment), although the peel-away sheath for this embodiment may be longer to accommodate the increased pre-delivery length of this embodiment, because the flexible graft portion 232 is not folded into the stent-graft portion 212 in the pre-delivery state.

The previously described delivery system and method of delivering the system may be used for this embodiment. Once within the blood vessel, the stent-graft portion 212 may be exposed from the delivery sheath and expanded radially outward and into engagement with the vessel wall. The mounting frame 60 and valve 30 will initially be located inferiorly from the stent-graft portion 212 after the stent-graft portion 212 has been expanded.

With the stent-graft portion 212 expanded, the flexible graft portion 232 and valve 30 will be pushed in a superior direction toward the heart, everting the flexible graft portion 232. The inferior section 232a will be pushed superiorly and disposed within the stent-graft portion 212, and the superior section 232b will be pushed superiorly beyond the inferior section 232a and the stent-graft portion 212, such that it is everted relative to the pre-delivery state and the valve 30 is disposed superiorly from the stent-graft portion 212. FIG. 15 illustrates the position of the various components of the prosthesis 212 after being delivered and the flexible graft portion 232 has been everted.

As described above, prior to full expansion of the valve 30, the mounting frame will allow blood to flow through the openings in the frame 60, such that blood may pass through superior section 232b and the inferior section 232a of the flexible graft portion 232 (and therefore through the stent-graft portion 212), and the blood may exit the inferior end of the inferior section 232a and the inferior end 216 of the stent-graft portion 212.

With the flexible graft portion 232 everted, the valve 30 may then be fully expanded as described above. The branch vessels may be cannulated over the wires 120 in the manner described above.

In each of the above described embodiments, the flexible graft portion 32/232 extends inferiorly from a junction 37/237 with the stent-graft portion 212, and the mounting frame 60 is easily accessible at the operator end of the system, and the valve 30 mounted thereto may be quickly and effectively deployed to the desired location by everting the flexible graft portion 32/232 attached to the stent-graft portion 12/212 after the prosthesis has been delivered into the body vessel. The stent-graft portion 12/212 is the first component exposed from the delivery sheath and the first component expanded within the blood vessel, and the flexible graft portion 32/232 is subsequently everted to transfer the valve 30 from its location near the operator end to a location superior from the stent-graft portion 212, in particular at a location of a damaged aortic valve where valve replacement is desired.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

What is claimed is:

1. A prosthesis for placement within a patient's vasculature, the prosthesis comprising:
 a pre-delivery configuration, a first delivered configuration, and a second delivered configuration, wherein the pre-delivery configuration is a configuration prior to delivery into the vasculature of a patient, and the first and second delivered configurations are configurations after delivery of the prosthesis to the vasculature of the patient, where the second delivered configuration succeeds the first delivered configuration;
 wherein, in the second delivered configuration, the prosthesis comprises:
 a graft portion having a superior end configured to lie closest to a heart of a patient in a body vessel and an inferior end configured to lie further from the heart of the patient in the body vessel, such that the superior end is an inflow end of the prosthesis in the second delivered configuration;
 a valve mounting frame at the superior end of the graft portion;
 at least one perfusion port between the superior and inferior ends of the graft portion;
 a stent graft portion extending from the inferior end of the graft portion in the second delivered configuration and having a stent graft superior end coincident with the inferior end of the graft portion to form a graft portion/stent graft portion junction, a stent-graft inferior end, an opening at the stent-graft inferior end, and an internal lumen, wherein in the second delivered configuration the inferior end of the stent graft is the outflow end of the prosthesis;
 wherein, in the pre-delivery configuration, the graft portion is inverted into the lumen of the stent graft portion such that the valve mounting frame is located at the inferior end opening of the stent graft portion and the prosthesis is in a compressed configuration; and
 wherein, in the first delivered configuration, the stent graft portion is expanded and the graft portion is in position to be everted out of the superior end of the stent graft portion after expansion of the stent graft portion.

2. The prosthesis of claim 1, wherein, in the first delivered configuration and the pre-delivery configuration, and prior to the eversion of the graft portion out of the superior end of the stent graft portion, at least a portion of the valve mounting frame extends out of the stent-graft portion from the inferior end opening of the stent-graft portion.

3. The prosthesis of claim 1, wherein the at least one perfusion port provides fluid communication radially through a sidewall of the graft portion to provide perfusion to an adjacent body vessel from the interior of the prosthesis in the second delivered configuration.

4. The prosthesis of claim 3, wherein, in the pre-delivery configuration and the first delivered configuration, the at least one perfusion port is disposed within the lumen of the stent-graft portion and, in the second delivered configuration, the at least one perfusion port is disposed outside of the lumen of the stent-graft portion and superior from the stent-graft portion to provide fluid communication between outside of the graft portion to inside of the graft portion and the lumen of the stent-graft portion.

5. The prosthesis of claim 3, further comprising at least one preloaded wire in the first delivered configuration extending into the stent-graft portion through the inferior end opening of the stent-graft portion radially between the stent-graft portion and the graft portion, through at least one passageway and the tubular sidewall of the graft portion, and out through the superior end opening of the graft portion and the superior end of the stent-graft.

6. The prosthesis of claim 1, wherein, in the second delivered configuration, the graft portion defines a graft portion lumen that connects to the lumen of the stent-graft portion to define an extended lumen.

7. The prosthesis of claim 1 further comprising a peel-away sheath that houses the stent-graft portion and graft portion in the pre-delivery configuration.

8. The prosthesis of claim 1, wherein a tubular sidewall of the graft portion has a first tubular surface and a second tubular surface extending between the superior and inferior ends of the graft portion and, in the first delivered configuration, the first tubular surface is radially inward from the second tubular surface and, in the second delivered configuration, the first tubular surface is radially outward from the second tubular surface.

9. The prosthesis of claim 1, further comprising an aortic valve connected to the valve mounting frame in the pre-delivery configuration.

10. The prosthesis of claim 9, wherein, in the second delivered configuration, the aortic valve is disposed at least partially within the tubular sidewall of the graft portion.

11. The prosthesis of claim 9, wherein the valve mounting frame defines at least one opening therethrough that provides fluid communication through the superior end of the graft portion in the first delivered configuration.

* * * * *